United States Patent
Kim (10) Patent No.: US 11,642,392 B2
(45) Date of Patent: May 9, 2023

(54) THERAPEUTIC AGENT OF UREMIA CONTAINING ALARIN AS THE MAIN INGREDIENT

(71) Applicant: JU TIDE CO., LTD., Seoul (KR)

(72) Inventor: Jong-Chul Kim, Yongin-si (KR)

(73) Assignee: JU TIDE CO., LTD., Seoul (KR)

( * ) Notice: Subject to any disclaimer, the term of this patent is extended or adjusted under 35 U.S.C. 154(b) by 86 days.

(21) Appl. No.: 17/400,629

(22) Filed: Aug. 12, 2021

(65) Prior Publication Data

US 2022/0031804 A1 Feb. 3, 2022

Related U.S. Application Data

(63) Continuation of application No. 16/758,022, filed as application No. PCT/KR2018/003601 on Mar. 27, 2018, now abandoned.

(30) Foreign Application Priority Data

Dec. 26, 2017 (KR) .......................... 10-2017-0179309

(51) Int. Cl.
*A61K 38/17* (2006.01)
*A61K 9/00* (2006.01)

(52) U.S. Cl.
CPC ........ *A61K 38/1709* (2013.01); *A61K 9/0019* (2013.01)

(58) Field of Classification Search
None
See application file for complete search history.

(56) References Cited

U.S. PATENT DOCUMENTS

2009/0149374 A1* 6/2009 Kofler .................... C07K 16/26
435/7.1

* cited by examiner

*Primary Examiner* — Ronald T Niebauer
(74) *Attorney, Agent, or Firm* — Vorys, Sater, Seymour and Pease LLP; Mih Suhn Koh (57) ABSTRACT

Provided is a novel use of alarin derived from a splice variant of galanin-like peptide (GALP) RNA and thus having an amino acid sequence similar to that of galanin, with a therapeutic agent of uremia, and the therapeutic agents of uremia according to the presently claimed subject matter include alarin as the main ingredient.

3 Claims, 5 Drawing Sheets

Specification includes a Sequence Listing.

THERAPEUTIC AGENT OF UREMIA CONTAINING ALARIN AS THE MAIN INGREDIENT

CROSS-REFERENCE TO RELATED APPLICATIONS

This application is a continuation of U.S. patent application Ser. No. 16/758,022, filed Apr. 21, 2020, which was a national stage of International Application No. PCT/KR20181003601, filed Mar. 27, 2018, which claims the benefit of Korean Application No. 10-2017-0179309, filed Dec. 26, 2017, in the Korean Intellectual Property Office, the disclosures of which are incorporated herein by reference.

SEQUENCE LISTING

The instant application contains a Sequence Listing which has been submitted electronically in ASCII format and is hereby incorporated by reference in its entirety. Said ASCII copy, created on Aug. 6, 2021, is named SequenceListing.txt and is 1,823 bytes in size.

TECHNICAL FIELD

The present invention relates to a therapeutic agent of uremia containing alarin as the main ingredient, and more particularly, to the use of alarin as a therapeutic agent of uremia with a new use of alarin derived from a splice variant of galanin-like peptide (GALP) RNA and having an amino acid sequence similar to galanin.

BACKGROUND ART

Despite of the development of medical technology, there are no effective method of treatments for many diseases yet, and such intractable diseases may include uremia. Uremia refers to a syndrome that shows various clinical symptoms resulting from abnormal expression for functions of various organs and tissues caused by harmful components of urine accumulated in blood, which are occurred when the urine cannot be discharged outside the body due to the breakdown of kidney function whatever the underlying disease. The clinical symptoms of uremia include, for example, digestive system abnormalities such as anorexia, nausea, vomiting, bad breath, stomatitis, enteritis, nervous system abnormalities such as indifference, indifference, decreased alertness, depressive state, nausea, lethargy, circulatory system abnormal such as anemia, red blood cell hematopoietic disorder, hypertension, ischemic heart disease, pericarditis, myocarditis and the like, and skin problems such as pigmentation, pruritus, subcutaneous bleeding, and uremia is caused by the urea toxin substance accumulated in the blood. There are various urea toxin substances, for example, methyl guanidine, indole compounds, malondialdehyde, creatinine, β-aminoisolactic acid, transketolase inhibitors, polyamines, urea, phenols, and the like. However, it is still unclear which of these urea substances are intrinsically involved in the development of uremic symptoms, and it is unknown whether uresis occurs only by a single substance or by a complex action of these plural substances. However, it is reported that the latter is most likely. These facts show dearly the difficulty of treating uremia with medicine. Whatever its development of occurrence, a person with uremia can face a fatal situation that leads to death, unless the urinary substance is released out of the body or the concentration of the urea in the blood is reduced by appropriate means. Up to date, therapies that are effective in the treatment of uremia include renal transplantation, dialysis and activated charcoal agent therapies, and the benefits of the latter two common treatments is that a plurality of urea toxin substances, including unknown materials by physical means can be removed or diluted nonspecifically.

However, activated charcoal agents are used as internal medicines, and the mechanism of action of activated charcoal agent is by adsorption and in vitro excretion of various toxic substances generated in the digestive organs. Thus, activated charcoal agent therapy is referred to as an internal medical agent, but like dialysis therapy it can also be regarded as a physical therapeutic means. In addition to that the activated charcoal agent is limited for therapeutic effect, there are several problems such as difficulty in taking them and a tendency to cause constipation, and thus it are not very satisfactory treatments.

On the other hand, dialysis is the most effective treatment for uremia, and in fact, when discharging the urea toxin substance in vitro by dialysis therapy, there is an advantage that the death of the patient due to the urea substance can be avoided even if the kidney function is abolished. However, complications caused by dialysis are becoming a new problem. These include, for example, the development of anemia, nephrotic dystrophy, kidney cancer, fibrinous pericarditis, aluminum osteopathy, amyloidosis, crystalline arthritis, multiple cysts, and the like as complications due to organ dialysis. In addition, there is a problem in the medical economy such as the low quality of the patients social life and the occurrence of high treatment costs that should visit frequently in the dialysis facility.

There has also been reported a method called "in vivo dialysis" in which non-proteinaceous nitrogen but not any physical method is transferred into the intestinal tract. It is the phenomenon that, when the 15-keto-16-halogen-prostaglandin E2 class is administered to the renal failure model rats, the blood serum creatinine (Cre) and blood urea nitrogen (BUN) are transferred to the organ together with the moisture by its ⌈enteropulling action (action which store a moisture in the digestive tract)⌋. However, the enteropulling action is an action of storing a moisture in the digestive tract, and therefore, it inevitably involves diarrhea and the reporter also mentions this point. Moreover, no matter how much blood serum Cre or BUN values are lowered, long-term treatment of this remedy which involves risk of physical depletion and dehydration due to diarrhea is very burdensome for patients with chronic renal failure and then is hard to be recognized as practically acceptable treatment.

Therefore, there is a demand for the creation of a treatment method of uremia or a therapeutic agent of uremia that does not have the above-described problems. To meet these needs, under the title of pharmaceutical composition useful for treating uremia, Korean patent publication No. 1989-0001535 (Patent Document 1) describes "the pharmaceutical composition containing a mixture of several salts of the basic α-amino and α-keto analog of the branched chain essential amino acid, the composition being characterized in that it is provided in the form of a gastric poorly solubility or gastric interoperability coating tablet".

However, the invention disclosed in the above Patent Document 1 still has a problem in that it is difficult to provide a satisfactory treatment effect for uremia, and thus there is still a need for a therapeutic agent having excellent treatment effect of uremia with long-term use without causing other side effects.

Meanwhile, alarin derived from a splice variant of galanin-like peptide (GALP) RNA is present in vivo by biosynthesis and synthesized with genetic engineering, which is a peptide having the amino acid sequence of APAH-RSSTFPKWVTKTERGRQPLRS (SEQ ID NO: 1). Since these alarin shares only 5 amino acids together with GALP, it cannot activate GALP specific receptors, and neuropeptides have been reported to be expressed in ganglion cells of human neuroblastoma tumors and may be potential tumor markers. For more details on such alarin, reference may be made to International Patent Publication No. WO/20061094973 (Patent Document 2), which are incorporated herein by reference in their entirety.

The above Patent Document 2 only proposes the use of alarin as a therapeutic agent for neurological keratitis, retinol disease, acute and chronic inflammatory and autoimmune diseases, obesity or growth deficiency, wound healing, uterine fibroids, endometriosis, and anorexia.

Therefore, the present inventors have recognized and studied to solve the above-mentioned conventional problems, and as a result, we found that a peptide that can be simply provided, alarin exerts an excellent improvement effect in cisplatin-induced uremia, while being the peptide present in the human body do not cause side effects of conventional therapeutic agents such as gastrointestinal disorders, liver disorders, renal disorders, and diarrhea so that can be used for a long time as a therapeutic agent for treating uremia, so the present invention can be completed by the said finding.

Technical Problem

Accordingly, it is a main object of the present invention to solve these problems of the prior art on the base of the background of the problems in the conventional uremic treatments described at the above. More specifically, an object of the present invention is to provide a therapeutic agent of uremia that is able to long-term use with providing a satisfactory treatment of uremia as a therapeutic substance that can be simply provided, while not causing side effects such as anemia, nephrotic dystrophy, endocarditis, aluminum osteopathy, amyloidosis, crystalline arthritis, multiple cysts, and diarrhea, and also incurring qualitative deterioration and high treatment costs in the social life of the patient.

Another object of the present invention is to provide a method which can more easily provide a therapeutic agent of uremia having the above-described characteristics.

The present invention may also be aimed at achieving, in addition to the above-mentioned specific objects, other objects that can be readily derived by those skilled in the art from the said objects and the overall description of the present specification.

Technical Solution

In order to achieve the above object, the present inventors have recognized the problems in the conventional treatment of uremia and have studied to solve them. As a result, we obtained the experimental data that the neuropeptide, alarm, which shares only 5 amino acids with GALP, has an excellent improvement effect in cisplatin-induced uremia, and then reveal that it was possible to provide a therapeutic agent of uremia, which is composed mainly of alanine from the said results, and thus the object of the present invention could be achieved.

The therapeutic agent of uremia according to the present invention for achieving the above object is characterized in that it comprises alarin as a main component.

According to another embodiment of the present invention, the alarin is characterized in that it is the human-derived alarin trifluoroacetate salt having the following amino acid sequence:

```
                                            (SEQ ID NO: 1)
    H-Ala-Pro-Ala-His-Arg-Ser-Ser-Thr-

Phe-Pro-Lys-Trp-Val-Thr-Lys-Thr-Glu-Arg-

Gly-Arg-Gln-Pro-Leu-Arg-Ser-OHtrifluoroacetate salt.
```

According to another embodiment of the present invention, the alarin has a molecular weight of 2894.29, characterized in that it has the following molecular formula:

$C_{27}H_{206}N_{43}O_{38}$

According to another embodiment of the present invention, the therapeutic agent of uremia according to the present invention is characterized in that it is formulated to be administered from 0.5 mg to 10 mg of alarin per an adult of 60 kg body weight.

According to another embodiment of the invention, the formulation is characterized in that it is an injectable one.

According to another embodiment of the invention, the formulation is characterized in that it is injected by subcutaneous muscle injection.

BRIEF DESCRIPTION OF THE DRAWINGS

The therapeutic agent of uremia containing alarin according to the present invention will now be described by way of example only, with reference to the accompanying drawings, in which.

DETAILED DESCRIPTION OF THE INVENTION

Hereinafter, preferred embodiments of the present invention will be described in detail.

The therapeutic agent of uremia according to a preferred embodiment of the present invention contains alarin as a main component.

According to another preferred embodiment of the present invention, alarin used as a therapeutic agent of uremia of the present invention may be human-derived alarin having the following amino acid sequence:

```
                                  (SEQ ID NO: 5)
Ala-Pro-Ala-His-Arg-Ser-Ser-Thr-Phe-Pro-

Lys-Trp-Val-Thr-Lys-Thr-Glu-Arg-Gly-

Arg-Gln-Pro-Leu-Arg-Ser-OH
```

According to another preferred embodiment of the present invention, alarin used as a therapeutic agent of uremia of the present invention may be a pharmaceutically acceptable salt of human-derived alarin having the said amino acid sequence.

By the said pharmaceutically acceptable salts are meant salts which retain the biological effects of the free acids and bases of specific compounds and are not biologically or otherwise harmful. The compounds of the present invention may have functional groups that are sufficiently acidic, sufficiently basic, or both, and thus can react with any of the number of inorganic or organic bases, and inorganic and organic acids to produce pharmaceutically acceptable salts. Exemplary pharmaceutically acceptable salts include salts prepared by reaction of a compound of the invention with an inorganic or organic acid or inorganic base, for example such as salts including trifluoroacetate, sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, cheverate, sebacate, fumarate, maleate, butane-1,4-dioleate, hexain-1,6-dioleate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycholate, tartrate, methanesulfonate, propanesulfonate, naphthalene-1-sulfonate, naphthalene-2-sulfonate and mandelate.

According to another preferred embodiment of the present invention, alarin used as a therapeutic agent of uremia of the present invention may be a human-derived alarin trifluoroacetate salt having the following amino acid sequence particularly:

```
                                  (SEQ ID NO: 1)
H-Ala-Pro-Ala-His-Arg-Ser-Ser-Thr-Phe-

Pro-Lys-Trp-Val-Thr-Lys-Thr-Glu-Arg-

Gly-Arg-Gln-Pro-Leu-Arg-Ser-OHtrifluoroacetate salt
```

According to another preferred embodiment of the invention, the said alarin has a molecular weight of 2894.29 and has the following molecular formula:

$C_{127}H_{206}N_{43}O_{38}$

According to another preferred embodiment of the present invention, the said alarin may be stored stably at −20±5° C.

According to another preferred embodiment of the present invention, the therapeutic agent of uremia of the present invention may be administered from 0.5 mg to 10 mg of alarin per adult of 60 kg body weight to provide a uremic treatment effect Preferably, the therapeutic agent of uremia of the present invention may be adminstered from 1.0 mg to 5.0 mg of alarin per adult of 60 kg body weight to provide a uremic treatment effect. More preferably, the therapeutic agent of uremia of the present invention may be administered from 2.0 mg to 5.0 mg of alarin per adult of 60 kg body weight to provide a uremic treatment effect. Even more preferably, the therapeutic agent of uremia of the present invention may be administered from 3.0 mg to 5.0 mg of alarin per adult of 60 kg body weight to provide a uremic treatment effect Most preferably, the therapeutic agent of uremia of the present invention may be administered from 4.0 mg to 5.0 mg of alarin per adult of 60 kg body weight to provide a uremic treatment effect.

According to another preferred embodiment of the present invention, the said therapeutic agent of uremia of the present invention may be formulated into formulations which is intended to be administered 0.5 mg to 10 mg, preferably 1.0 mg to 5.0 mg, more preferably 2.0 mg to 5.0 mg, even more preferably 3.0 mg to 5.0 mg, and most preferably 4.0 mg to 5.0 mg of alarin based on an adult of 60 kg body weight to provide a uremic treatment effect.

According to another preferred embodiment of the present invention, the said formulation may be preferably, but not particularly limited to, an injection.

According to another preferred embodiment of the present invention, the said formulation may be preferably, but not particularly limited to, an injectable one injected by subcutaneous muscle injection.

According to another preferred embodiment of the present invention, when the therapeutic formulation of the present invention is an injection, a solvent, solubilizing agent or emulsifying agent is used as the carrier component, such as water, ethanol, isopropanol, ethyl carbonate, ethyl acetate, benzyl alcohol, benzyl benzoate, propylene glycol, 1,3-butylglycol oil, glycerol aliphatic esters, polyethylene glycols or fatty add esters of sorbitan.

Hereinafter, the present invention will be described in more detail with reference to preferred examples, but the present invention is not limited to these examples.

Example

Cisplatin-induced uremia was evaluated for the effect of administration of test substance on an improvement of uremia in the Sprague-Dawley rat model. Here, G1 is normal control group which is administered with an excipient, G2 is induced control group which is administered with an excipient, G3 is group which test substance is administered with 10 μg/1 mL/head, and G4 is group which test substance is administered with 20 μg/1 mL/head. Here, test substance is alarin (human) trifluoroacetate salt of the present invention. Cisplatin was intraperitoneally administered (IP) and test substance was intravenously administered (IV).

In addition, the test substance (G3-G4) was administered once at 8 hours (Day 0) after cisplatin administration, and in the case of cisplatin (G2-G4), dose of 5 mg/10 mL/Kg was administered once at 8 hours (Day 0) before test substance administration.

The intravenous administration was done by fixing an animal into a correction frame, and slowly injecting at a rate of within 1 mL/min through the micro vein using a syringe equipped with 26 gauges needle. The intraperitoneal administration was performed by fixing the animal by a transdermal skin fixation method and intraperitoneally injecting using a syringe equipped with 26 gauges needle.

Body weights were measured on the day of administering test substance, inducing and necropsy (Day 7). As a result, the weight level of all the test substance-administered groups measured on the day of necropsy showed no significant difference from the normal control group.

Figure 1:
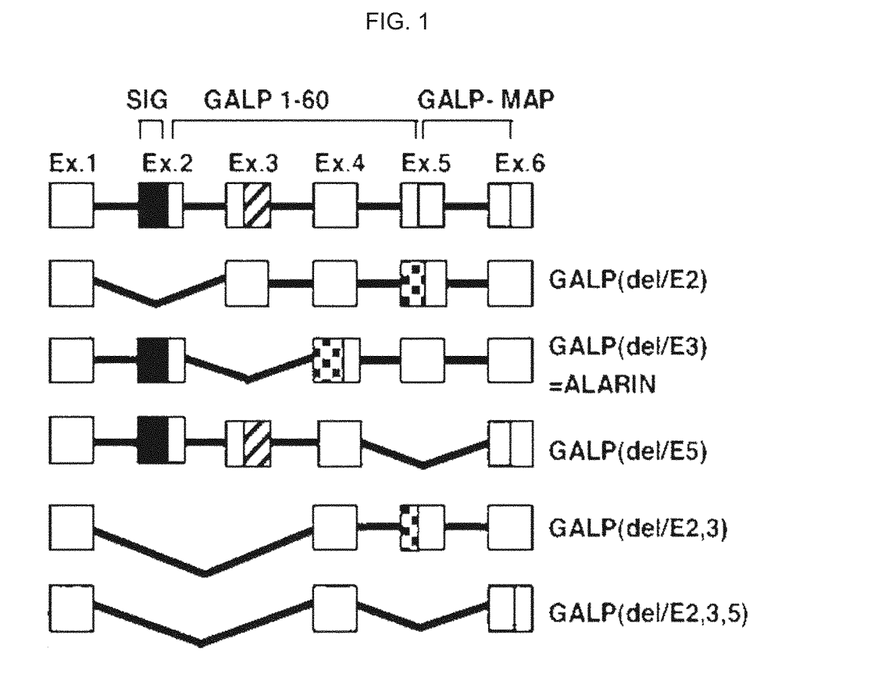
FIG. 1 shows gene splice variants of galanin-like peptides (GALPs) derived from Murine.
Figure 2:
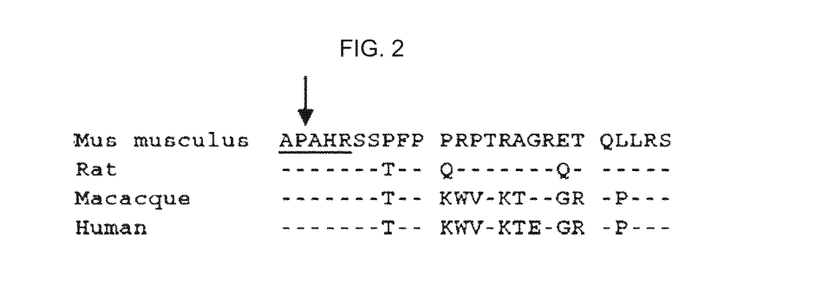
FIG. 2 shows the results of comparing the amino add sequences of alarin obtained from murine (SEQ ID NO: 2), rats (SEQ ID NO: 3), macaques (SEQ ID NO: 4) and humans (SEQ ID NO: 5) according to a preferred embodiment of the present invention.
Figure 3:
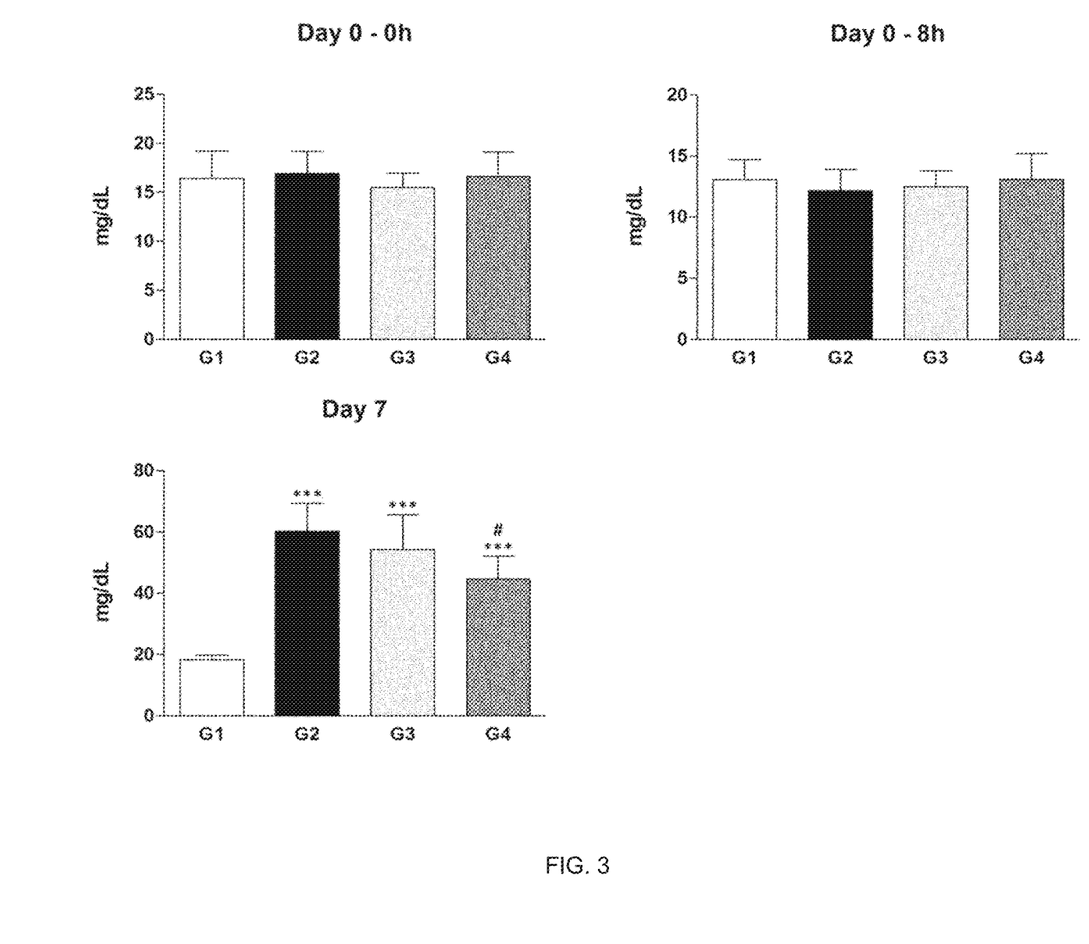
FIG. 3 is a graph showing the concentration of blood urea nitrogen (BUN) in the control group and the group administered the therapeutic agent of the present invention in Sprague-Dawley rat model having a cisplatin-induced uremia according to example of the present invention.
Figure 4:
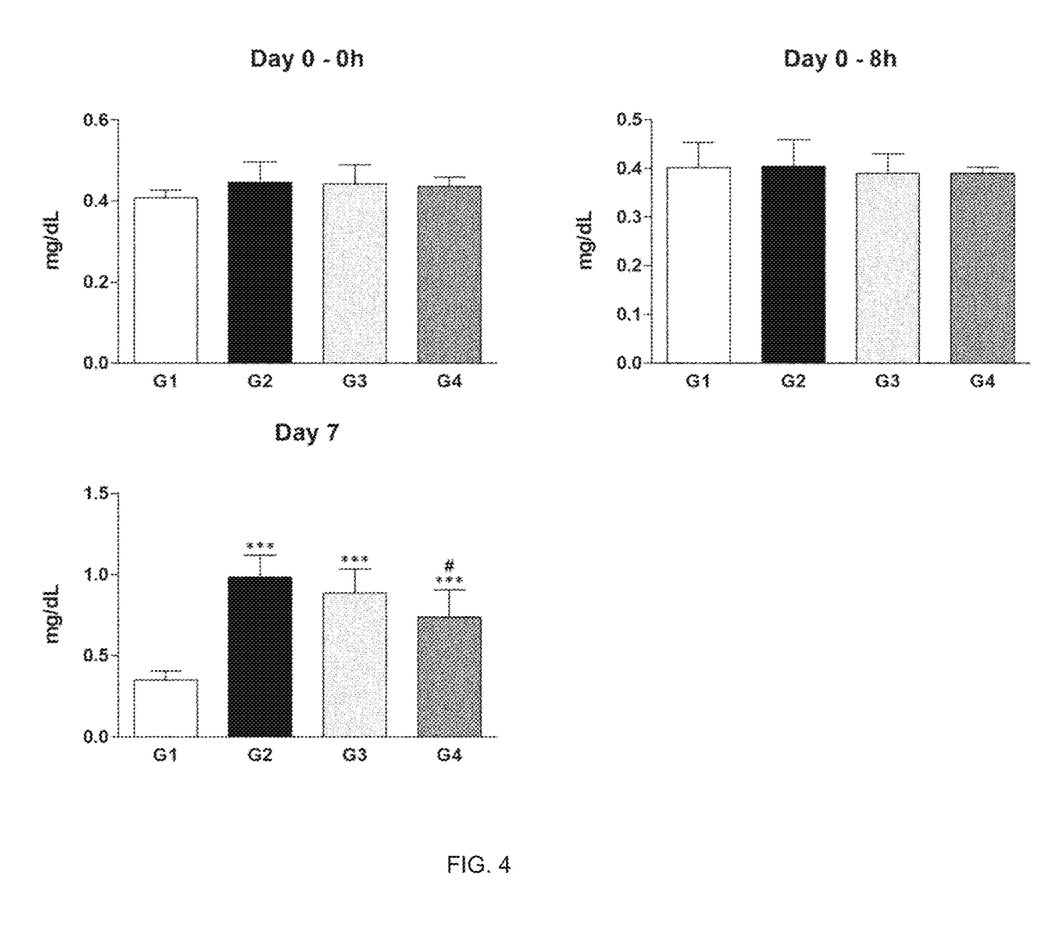
FIG. 4 is a graph showing the concentration of creatinine (CRE) in the control group and the group administered the therapeutic agent of the present invention in Sprague-Dawley rat model having a cisplatin-induced uremia according to example of the present invention.

In addition, blood is collected from the jugular vein of al living animals prior to administration of the test substance, before administration of cisplatin, and necropsy, injected into a tube containing a coagulation activator, and allowed to coagulate with standing at room temperature for about 15 minutes, followed by centrifugation at 3,000 rpm for 10 minutes. Serum obtained from the centrifugation was tested for blood urea nitrogen (BUN) and creatine (CRE) using a blood biochemical analyzer (7180 Hitachi, Japan). The blood biochemical test results showed significantly lower BUN and CRE levels in the high dose group of the test substance than the induced control group.

Figure 5:
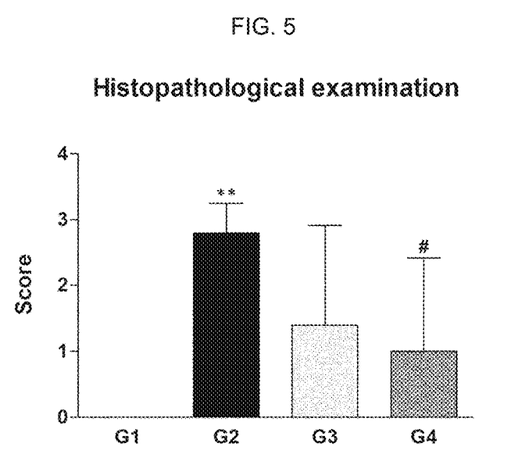
FIG. 5 is a graph showing the histopathological assay results in the control group and the group administered the therapeutic agent of the present invention in Sprague-Dawley rat model having a cisplatin-induced uremia according to example of the present invention, wherein one point is less than 25% of coronary necrosis at the junction site between the cortex and the cerebral cortex, two points are from 25% to 50% of coronary necrosis, three points are from 50% to 75% of coronary necrosis, and 4 points are greater than 75% of coronary necrosis.
Figure 6:
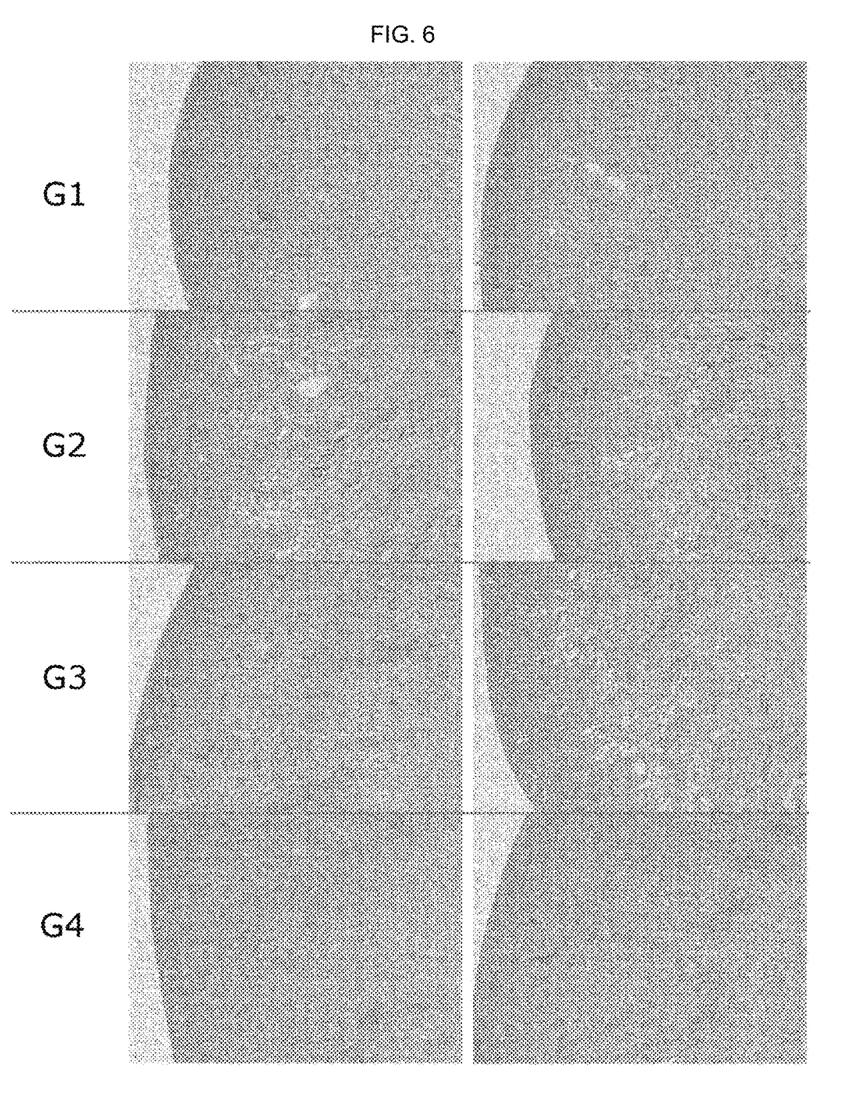
FIG. 6 is a graph showing the micrograph of histopathological assay results in the control group and the group administered the therapeutic agent of the present invention in Sprague-Dawley rat model having a cisplatin-induced uremia according to example of the present invention.

Finally, animals were inhaled with ether on an necropsy day to anesthetize and euthanize, and kidneys were extracted and fixed in a 10% neutral buffered formalin solution, and the fixed tissues were cut, dehydrated, paraffin embedded and hematoxylin & eosin stained to make a specimens for histopathological examination after these histological treatment. And then, the obtained specimen is subjected to speculum using an optical microscope (Olympus BX53, Japan). Histopathological examination showed that the level of lesion in the high dose group of test substance was significantly lower than that of the control group.

Therefore, when the test substance is administered with a single dose of 10 μg/1 mL/head and 20 μg/1 mL/head in a Sprague-Dawley rat model in which uremia was induced by administration of cystine under these test conditions, a tendency to improve the blood biochemical level in the group of test substance being compared to the control group of excipient was observed, and in particular, the BUN and CRE levels of the test substance of 20 μg/1 mL/head showed a significant difference compared to the control group of excipient. In addition, the histopathological examination results showed a dose-related change trend and significant changes in lesion level. Therefore, alarin of the present invention is believed to have an effect on the improvement of uremia in cisplatin-induced uremia model.

Advantageous Effects

Since the therapeutic agent of uremia containing alarin as the main ingredient of the present invention which is constituted as described above is mainly composed of alarin which is a kind of peptide that is present in vivo and can be simply synthesized, it can be easily provided and shows an excellent uremic treatment effect but also does not occur side effects such as anemia, nephrotic dystrophy, epicarditis, aluminum osteopathy, amyloidosis, crystalline arthritis, multiple cystic vesicles, diarrhea, and also does not cause qualitative deterioration in the patient's social life and high incidence of treatment costs accompanied with treatment, thereby providing an excellent anti-uremic treatment agent that can be used for a long time, and providing an excellent effect to solve the problems associated with the conventional treatment of uremia.

What is claimed is:

1. A method of treating uremia comprising administering to a subject in need thereof a pharmaceutical composition comprising alarin as an active ingredient, wherein the alarin is a human-derived alarin trifluoroacetate salt having the amino acid sequence: H-Ala-Pro-Ala-His-Arg-Ser-Ser-Thr-Phe-Pro-Lys-Trp-Val-Thr-Lys-Thr-Glu-Arg-Gly-Arg-Gln-Pro-Leu-Arg-Ser-OH-trifluoroacetate salt (SEQ ID NO: 1).

2. The method of claim 1, wherein the composition is administered by injection.

3. The method of claim 2, wherein the injection is subcutaneous muscle injection.

* * * * *

SEQUENCE LISTING

```
<160> NUMBER OF SEQ ID NOS: 5

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Pro Ala His Arg Ser Ser Thr Phe Pro Lys Trp Val Thr Lys Thr
1               5                   10                  15

Glu Arg Gly Arg Gln Pro Leu Arg Ser
            20                  25

<210> SEQ ID NO 2
<211> LENGTH: 25
<212> TYPE: PRT
<213> ORGANISM: Mus musculus

<400> SEQUENCE: 2

Ala Pro Ala His Arg Ser Ser Pro Phe Pro Pro Arg Pro Thr Arg Ala
1               5                   10                  15

Gly Arg Glu Thr Gln Leu Leu Arg Ser
            20                  25

<210> SEQ ID NO 3
<211> LENGTH: 25
<212> TYPE: PRT
```

```
<213> ORGANISM: Rattus sp.

<400> SEQUENCE: 3

Ala Pro Ala His Arg Ser Ser Thr Phe Pro Gln Arg Pro Thr Arg Ala
1               5                   10                  15

Gly Arg Gln Thr Gln Leu Leu Arg Ser
            20                  25

<210> SEQ ID NO 4
<211> LENGTH: 25
<212> TYPE: PRT
<213> ORGANISM: Macaca sp.

<400> SEQUENCE: 4

Ala Pro Ala His Arg Ser Ser Thr Phe Pro Lys Trp Val Thr Lys Thr
1               5                   10                  15

Gly Arg Gly Arg Gln Pro Leu Arg Ser
            20                  25

<210> SEQ ID NO 5
<211> LENGTH: 25
<212> TYPE: PRT
<213> ORGANISM: Homo sapiens

<400> SEQUENCE: 5

Ala Pro Ala His Arg Ser Ser Thr Phe Pro Lys Trp Val Thr Lys Thr
1               5                   10                  15

Glu Arg Gly Arg Gln Pro Leu Arg Ser
            20                  25
```